United States Patent [19]
Elias et al.

[11] Patent Number: 5,885,565
[45] Date of Patent: *Mar. 23, 1999

[54] METHODS FOR INDUCING PHASE SEPARATION OF EPITHELIAL LIPID BILAYERS

[75] Inventors: Peter M. Elias, Muir Beach; Stephen Grayson; Carl R. Thornfeldt, both of San Rafael, all of Calif.

[73] Assignees: Cellegy Pharmaceuticals Inc., Foster City; The Regents of the University of California, Oakland, both of Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 638,302

[22] Filed: Apr. 26, 1996

Related U.S. Application Data

[60] Division of Ser. No. 261,343, Jun. 16, 1994, abandoned, which is a continuation-in-part of Ser. No. 33,807, Mar. 19, 1993, abandoned.

[51] Int. Cl.$^6$ ...................................................... A61K 9/06
[52] U.S. Cl. .......................... 424/78.02; 424/46; 424/433; 424/DIG. 15; 514/969; 514/937; 514/944; 514/936; 514/947
[58] Field of Search .................................. 424/43, 78.02, 424/46, 433, DIG. 15; 514/937, 946, 947, 969, 944, 936

[56] References Cited

U.S. PATENT DOCUMENTS 4,177,267 12/1979 Herschler .
5,073,372 12/1991 Turner et al. .
5,215,759 6/1993 Mausner .

*Primary Examiner*—Raj Bawa
*Attorney, Agent, or Firm*—Townsend and Townsend and Crew LLP

[57] ABSTRACT

A method for enhancing penetration of a therapeutic or prophylactic agent in a host in need of the topical administration thereof which comprises applying to the epithelium of the host, an effective amount of one or more penetration enhancing epithelial sterols and the therapeutic or prophylactic agent.

12 Claims, 4 Drawing Sheets

METHODS FOR INDUCING PHASE SEPARATION OF EPITHELIAL LIPID BILAYERS

This is a divisional of application Ser. No. 08/261,343 filed Jun. 16, 1994 now abandoned which is a continuation-in-part application of U.S. Ser. No. 08/033,807, filed Mar. 19, 1993, now abandoned.

BACKGROUND OF THE INVENTION

1. Field of the Invention

This invention relates to a method for enhancing permeation of topically administered physiologically active agents by inducing phase separation of stratum corneum intercellular lipid bilayers in epidermis and keratinized mucous membrane.

2. Description of the Related Art

The major function of epithelia, including the stratum corneum of epidermis and of keratinizing mucous membranes, is to prevent the excessive loss of bodily fluids. If the epithelial barrier function is disrupted or perturbed, it stimulates a variety of metabolic changes in the epidermis and mucous membranes leading to repair of the barrier defect. While the barrier is beneficial for protection against damage from ultraviolet radiation, desiccation, chemical, frictional, and blunt trauma, it also impedes the percutaneous and transmucosal penetration of topically applied medicaments of potential benefit to the host. The inability of physiologically active agents to penetrate the epithelium significantly limits their effective use for treating disease conditions and disorders not only of the skin and mucosae, but also of a systemic nature.

The epithelial barrier resides in a system of multilayered lipid bilayers that exist throughout the stratum corneum and keratinized mucous membrane intercellular spaces. These lipid bilayers in the stratum corneum contain three major lipid components: ceramides, free fatty acids, and cholesterol, present in an approximately equimolar ratio and, in addition, a small, but critical, quantity of acylceramides. These lipid bilayers in the keratinized mucous membrane contain glucosylceramide instead of ceramide and acylceramide.

In addition to the long-standing approaches of hydration and occlusion, currently available percutaneous and transmucosal penetration enhancement technology relies on physical-chemical methods, such as solvents or detergents, and physical approaches, such as iontophoresis, electroporation, or sonophoresis. Typical solvents or detergents alter the physical properties of intercellular membrane bilayers. Such agents include dimethylsulfoxide (DMSO), oleyl alcohol (OA), propylene glycol, methyl pyrrolidone and AZONE® (dodecyl azyl cycloheptan 2-one). For example, U.S. Pat. No. 4,177,267 discloses topical steroid compositions containing dimethylsulfoxide as an epithelial penetration enhancer. It is generally believed that many of these epithelial penetration enhancers fluidize the polar head group (e.g., DMSO) and/or nonpolar tail group (e.g., OA) domains within the membrane bilayers. Yet, some compounds with significant fluidizing effect have been shown to be incapable of substantially increasing epithelial permeability. While these methods typically enhance penetration of certain compounds by three- to five-fold, these methods are only relatively effective for smaller lipophilic and amphiphathic molecules. Hydrophilic compounds such as proteins or peptides do not penetrate in pharmaceutically useful quantities through the epithelia by most of these methods.

Accordingly, there is a definite need for improved epithelial permeation enhancers which allow the penetration of physiologically active molecules in sufficient quantities. This invention addresses this need by providing a method and topical composition for penetration enhancement via phase separation of the stratum corneum and mucous membrane intercellular lipid bilayers by percutaneous or transdermal delivery.

SUMMARY OF THE INVENTION

This invention is based on the finding that the phase separation of stratum corneum and mucous membrane intercellular lipid bilayers can be induced by several mechanisms, and that the epithelial penetration of a given physiologically active substance can occur and/or be substantially improved once such intercellular phase separation has been affected.

In one aspect thereof, this invention provides a method for inducing phase separation of epithelial intercellular lipid bilayers in a host in need of topical administration of a physiologically active substance delivered percutaneously or transdermally, which comprises applying to the skin or mucosa of the host an effective amount of an intercellular phase-separating agent.

In another aspect, this invention provides a topical composition for inducing phase separation of stratum corneum intercellular lipid bilayers of the epidermis and of the keratinized mucous membrane in a host in need of topical administration of a physiologically active substance delivered percutaneously or transdermally, which comprises an effective amount of an intercellular phase-separating agent, together with a physiologically acceptable carrier delivered percutaneously or transdermally.

In a further aspect, this invention provides a method for enhancing the percutaneous, transmucosal and transdermal penetration of a physiologically active substance in a host in need of topical administration of the substance, which comprises applying to the skin or mucosa of the host an effective amount of an intercellular phase-separating agent.

The above features and advantages of this invention will be more fully understood by reference to the following detailed description.

BRIEF DESCRIPTION OF THE DRAWINGS

FIG. 1 shows TEWL when animals were treated with acetone followed by HEPES with variable pHs.

FIG. 2 shows TEWL when animals were treated with acetone followed by PIPES with variable pHs.

FIG. 3 shows TEWL when animals were treated with acetone followed by sodium phosphate with variable pHs.

FIG. 4 shows TEWL when animals were treated with acetone followed by DCCD.

FIG. 5 shows TEWL when animals were treated with acetone followed by DCCD.

FIG. 6 shows TEWL when animals were treated with acetone followed by DCCD.

FIG. 7 shows TEWL when animals were treated with acetone followed by NEM, NBD-chloride or BAF.

DETAILED DESCRIPTION OF THE INVENTION

Intercellular phase separation occurs when the capacity of the multilayered lipid bilayers to take up excess quantities of exogenous lipids or other fluidizing molecules is exceeded.

As a result, spaces form when the multilayered lipid bilayers are pushed apart or to one side, thus, separating them within the intercellular spaces. These spaces extend and coalesce until significant spaces are present within and between the lipid bilayers within the intercellular spaces (i.e., phase separation), thus, disrupting barrier integrity.

According to the invention, phase separation can be induced by any one or more of the following mechanisms:

(1) accumulation of excessive amounts of one or more epithelial sterols, esters or salts or precursors thereof;
(2) accumulation of biosynthetic precursors of one or more of the epithelial sterols, esters, or salts or precursors thereof;
(3) substitution of non-physiologic analogs for any of the epithelial sphingolipids, sterols, esters, salts, or precursors thereof;
(4) modulation of epithelial pH with a biological pH modifier, which results in the accumulation of lipid biosynthetic precursors.

The method of this invention principally employs an effective amount of one or more of these epithelial intercellular phase separating agents.

As used herein, the term "an intercellular phase separating agent" means any compound which would fall within the above-referenced categories.

The term "epithelial sphingolipids" includes, among others, ceramides, acylceramide, glucosylceramides, and sphingomyelin.

The term "epithelial sterols, esters and salts thereof" includes, among others, cholesterol, cholesterol sulfate, and cholesteryl sulfate.

As used herein, the term "an effective amount" means that the amount of the intercellular separating agent is applied topically in sufficient quantities to induce phase separation and to enhance epithelial permeation of a given physiologically active substance to a desired degree in the skin or vasculature. The amount can vary according to the effectiveness of each phase separating agent, the depth of cutaneous penetration, the age, and response of the individual host, etc. More importantly, the amount should be determined based on the skin or mucosa penetration efficiency of a physiologically active substance when the substance is administered together with a phase-separating agent. The required quantity to be employed in this invention can be determined readily by those skilled in the art.

The term "penetration enhancement" or "permeation enhancement" as used herein relates to an increase in the permeability of the epithelium to a physiologically active substance; i.e., so as to increase the rate at which the substance permeates through the epithelial barrier. The substance may be targeted to remain within any of the subjacent layers of the skin or mucosa or may later enter the bloodstream of a host.

As used herein, the term "host" includes humans and non-human mammals. Non-human mammals of particular interest are domesticated species such as dogs, cats, monkeys, cows, horses, llamas, sheep, pigs, and goats.

As applied in this invention, the term "physiologically active substance" is intended to encompass any substance that will produce a physiological response when topically administered to a host. In general, the terms include therapeutic or prophylactic agents in all major therapeutic/prophylactic areas of medicine as well as nutrients, cofactors, and xenobiotics. Suitable substances include, but are not restricted to, antifungals such as amphotericin B, griseofulvin, miconazole, ketoconazole, tioconazole, itraconazole, and fluconazole; antibacterials such as penicillins, cephalosporins, tetracyclines, aminoglycosides, erythromicin, gentamicins, polymyxin B; anti-cancer agents such as 5-fluorouracil, bleomycin, methotrexate, hydroxyurea; anti-inflammatories such as glucocorticoids, including hydrocortisone, colchicine; nonsteroidal antiinflammatory agents including ibuprofen, indomethacin, and piroxicam; antioxidants, such as tocopherols, carotenoids, metal chelators, ubiquinones, or phytate; antihypertensive agents such as prazosin, verapamil, nifedipine, and diltiazem; analgesics such as acetaminophen and aspirin; antiviral agents such as acyclovir, ribavarin, and trifluorothyridine; antiandrogens such as spironolactone; androgens such as testosterone; estrogens such as estradiol; progestins such as modified progestogens; opiates; muscle relaxants such as papaverine; vasodilators such as nitroglycerin; antihistamines such as cyproheptadine; antitussives such as dextromethorphan; neuroleptics such as clozaril; antiarrhythmics; antiepileptics; proteins, polypeptides, neuropeptides such as somatostatin, substance P, vasoactive intestinal peptide (VIP), calcitonin-gene related peptide (CGRP), capsaicin, insulin, and gastrin; and protein enzymes, such as superoxide dismutase or neuroenkephalinase or psychotropics including penothiazines and tricyclics, carbohydrates, glycoproteins, glycolipids, other lipids and cytokines. Cytokines include tumor necrosis factors, the interleukins, growth factors, colony stimulating factors, and interferons. Other useful drugs, in approved commercially available formulations, and their recommended dosages are listed in the annual publication of the Physicians' Desk Reference, published by Medical Economics Company, a division of Litton Industries, Inc.

More than one physiologically active substance may be included, if desired, in the topical composition of this invention. The active substance will be present in the composition in an amount sufficient to provide the desired physiological effect with no apparent toxicity to the host. Of course, the appropriate dosage level of the physiologically active substance, without the use of the intercellular phase-separating agents of the present invention, are known to one skilled in the art. These conventional dosage levels correspond to the upper range of dosage levels for compositions, including a physiologically active substance and an intercellular phase-separating agent. However, because the delivery of the active substance is enhanced by the intercellular phase separation agents of this invention, dosage levels significantly lower than a conventional dosage level may be used with success. In general, the active substance will be present in the composition in an amount from about 0.0001% to about 60%, more preferably about 0.01% to about 20% by weight of the total composition depending upon the particular substance employed.

As indicated earlier, the amount of the intercellular phase separating agent present in the composition will depend on a number of factors. However, generally the amount will range from about 0.01 to about 25% by weight of the total composition, with levels of from about 0.05 to about 10% being preferred.

In one embodiment, the intercellular phase-separating agents useful in the compositions and methods of the present invention include any epithelial sterol, esters, salts, or precursors thereof and nonphysiologic analogs thereof. Cholesterol accounts for 20–25% of the stratum corneum lipids by weight.

In another embodiment, the intercellular phase-separating agents can be biosynthetic precursors of the epithelial sterols. Preferred precursors include squalene, 7-dehydrocholesterol, lanosterol, desmosterol, zymosterol, cholesterol sulfate, and cholesterol esters.

In a further embodiment, the intercellular phase-separating agents can be inactive synthetic (nonphysiologic) analogs of the epithelial sphingolipids including stearylamine and sterols, esters, and salts and precursors thereof, including epicholesterol and cholesterol phosphate. This embodiment also comprises combination of two or more of these anlogs combined with a synthetic fatty acid analog such as transvaccenic acid.

In a preferred embodiment, the intercellular phase separating agents can be biological pH modifiers. As used herein, the term "biological pH modifiers" includes both physiologically acceptable buffers, proton pump inhibitors, and granule secretion inhibitors. Suitable buffers act as a proton acceptor in vivo. Tris(hydroxymethyl) aminomethyl maleate (often referred to as TRIS), (N-[2-Hydroxyethyl] piperazine-N'-[2-ethanesulfonic acid]) (often referred to as HEPES), piperazine-N,N'-bis[2-ethanesulfonic acid (often referred to as PIPES), morpholine sulfonic acid (often referred to as MES) and 1,4-piperazine-diethanesulfonic acid are preferred. TRIS, HEPES, and MES are most preferred. Other organic amines such as tri(hydroxymethyl)aminomethane (THA), 2,4,6-trimethylpyridine and 2-amino-2-methyl-1,3-propanediol can be used. Suitable proton pump inhibitors include ionophores such as monensin, lasalocid, chloroquine, nigericin, valinomycin, gramicidin D, and salinomycin. Other preferred proton pump inhibitors are n-ethylmaleimide (NEM), N,N'-dicyclohexylcarbodiimide (DCCD), NBD-chloride, and bafilomycin (BAF) $A_1$ or $B_1$. The suitable inhibitor for proton bearing lamellar body secretion is brefeldin A. A list of inhibitors and their inhibited enzymes is found in Table 1 below.

TABLE 1

| Inhibitor | Code | Inhibited Enzyme | Critical Lipid Metabolic Pathway |
|---|---|---|---|
| Epicholesterol | EP | Non-metabolizable | Phase Separation |
| Transvaccenic Acid | TVA | " | " |
| Stearylamine | STA | " | " |
| N-([2-Hydroxyethyl]-piperazine-N'-[2-ethanesulfonic acid]) | HEPES | Buffer | Acidification |
| Tris(hydroxymethyl) aminomethyl maleate | TRIS | " | " |
| Monensin | MON | Proton Pump | " |
| Dicyclohexyl-carbodimide | DCCD | " | " |
| Brefeldin A | BFA | Granule Secretion | " |

Some of such proton pump inhibitors and buffers are disclosed in U.S. Pat. No. 5,130,139, the disclosure of which is incorporated by reference. The disclosed compounds therein inhibit the accumulation of skin-irritating drugs in the lysosome. The skin-irritating drugs are defined as weakly basic drugs which have at least one pKa greater than 4.5.

The drugs tend to accumulate in cellular lysosomes and cause skin irritation. However, there are neither teachings nor suggestions in the disclosure which relate to epithelial penetration enhancement by those pH modifiers. This invention is applicable not only to the weak base drugs as taught in U.S. Pat. No. 5,130,139, but also to non-irritating drugs outside the scope thereof. Hence, the use of the biological pH modifiers is particularly useful for the penetration enhancement of non-irritating drugs of therapeutical value.

While the buffers neutralize the acidic environment of the epithelial extracellular spaces and increase its pH, the "proton pump inhibitors" block the delivery to and/or confine proton equivalents to the intercellular spaces, thus precluding the intercellular pH from lowering. Glucocerebrosides and phospholipids are converted to ceramides and free fatty acids, respectively, by enzymatic hydrolysis in the acidic environment of the stratum corneum. In mucous membranes, phospholipids are converted to free fatty acids by this mechanism. At a pH of 6.0 or higher, this enzymatic hydrolysis ceases, which leaves the non-metabolized lipid precursors intact. The accumulation of these precursor molecules leads to phase separation. Thus, in an alkaline or neutral environment, the correct final proportion of free fatty acids, ceramides or glucosylceramides, and cholesterol, required for the formation of lipid bilayer structures that mediate epithelial barrier function, will not be generated. An effective amount of the biological buffers to be included in the composition of this invention should be sufficient to bring the intercellular pH of the epithelium to greater than 6.0.

Topical treatment regimens according to the practice of this invention comprise applying the composition directly to the skin or mucosa, i.e., at the application site, from one to several times daily. Any one of the above-indicated intercellular phase separating agents permits the significantly improved topical application of the physiologically active substance in terms of epithelial permeation. However, more than one intercellular phase-separating agent can be co-applied to the skin or mucosa of a host in a combined formulation. Alternatively, they can be applied concurrently as separate formulations if such combination synergistically enhances percutaneous or transmucosal absorption. Still further, one agent can be applied before or after application of the other agent(s) provided that the time interval between the two (or three) is not too lengthy, i.e., not more than a few hours. The physiologically active substance can be co-administered to the host with the topical compositions which contain one or more of the intercellular phase separating agents. Alternatively, the active substance may be administered after application of the topical composition. It is, however, for convenience to the host and the prescribing physician who prescribe medicaments to use the physiologically active agent and the intercellular phase separating agents as a single composition formulation.

Preferably and conveniently, the single or combined intercellular phase separating agent is applied to the skin or mucosa in combination with a physiologically acceptable carrier. The carrier may comprise any one of conventional topical formulation bases such as those described in Remington's "Pharmaceutical Sciences," 17th Edition (Mack Publishing Co., Pa). A lotion, solution, cream, gel, ointment, paste, aerosol, suppository, and nebulized formulation are representative of the topical compositions of this invention.

Other penetration-enhancing compounds are described in U.S. Pat. Nos. 4,424,210 and 4,316,893, the disclosures of which are incorporated by reference. Preferred penetration-enhancing compounds include 1-dodecylazacycloheptan-2-one (AZONE®) (Stoughton, Arch. Dermatol., 1982, 118), DMSO, propylene glycol, oleyl alcohol, and methyl pyrrolidone. The use level of the additional penetration-enhancing compounds is not significantly different from that of the intercellular phase-separating agents, and is in the range of from about 0.1 to about 10% and preferably about 1.0% to about 5.0% by weight of the topical composition.

Additional ingredients may be added to the topical composition, as long as they are pharmaceutically acceptable and not deleterious to the epithelial cells or their function. Further, they should not adversely affect the epithelial penetration efficiency of the above-noted intercellular phase separating agents, and should not cause deterioration in the stability of the composition. For example, fragrances, opacifiers, antioxidants, gelling agents, stabilizers, surfactants, emollients, coloring agents, preservatives, buffering agents, and the like may be present. The pH of the topical composition of this invention may be adjusted to a physiologically acceptable range of from about 6.0 to about 9.0 by adding buffering agents thereto in order for the composition to be physiologically compatible with the skin.

The effectiveness of the topical compositions of this invention to enhance epithelial penetration of a physiologically active substance at the desired site of a host is determined by their ability to induce intercellular phase separation.

The enhanced permeation effected through the use of the enhancer composition of this invention can be observed by measuring the rate of diffusion of the active agent through animal or human epithelium using a diffusion cell apparatus or the Fourier transform infrared spectroscopy (FTIR) technique known to one skilled in the art.

While the present invention has been described with respect to preferred embodiments thereof, it will be understood that various changes and modifications will be apparent to those skilled in the art, and that it is intended that the invention encompass such changes and modifications as falling within the scope of the appended claims. The following non-limiting examples are provided to further illustrate the present invention.

EXAMPLE 1

A lotion may be formulated as follows to contain about 0.1% to 2.0% estradiol valerate:

| | |
|---|---|
| Estradiol valerate | 1–10 g |
| Cetyl Alcohol | 200 g |
| Propylene glycol | 100 g |
| Sodium lauryl sulfate | 15 g |
| Epicholesterol | 10 g |
| Water | 400 cc |

EXAMPLE 2

An ointment may be formulated to contain 0.2% indomethacin:

| | |
|---|---|
| Indomethacin | 1 g |
| Propylene glycol | 500 cc |
| Carboxyvinyl polymer 940 | 1 g |
| Triethanolamine | 0.5 g |
| Squalene | 1 g |

EXAMPLE 3

A cream may be formulated as follows to contain about 0.1% nifedipine:

| | |
|---|---|
| Nifedipine HCl | 0.5 g |
| Cetyl alcohol | 100 g |
| Stearyl alcohol | 100 g |
| Polysorbate 80 | 20 cc |
| Monensin | 1 g |
| Water | 250 cc |

EXAMPLE 4

A suppository formulation may be prepared as follows to contain about 0.5% oxymorphone:

| | |
|---|---|
| Oxymorphone | 2.75 g |
| Polyethylene glycol 4000 | 400 g |
| Propylene glycol monostearate | 100 g |
| HEPES | 5 g |

EXAMPLE 5

TEWL (TRANSEPIDERMAL WATER LOSS) IMMERSION STUDIES

Hairless mice were treated with acetone on one flank to produce TEWL readings between 2.0 and 8.0 mg/cm$^2$/hr. The mice were injected with chloral hydrate to immobilize them, and the flanks were immersed in buffers, at 37° C., of varying pH (e.g., pH 5.5, 7.4 and 8.5). The buffers: 10 mM HEPES, 10 mM PIPES, and 100 mM sodium phosphate included 280 mosmolar sucrose. The TEWL 0 time point was taken soon after acetone treatment when the treated flank returned to ambient temperature (approximately 10 minutes with gentle heating). Time points at 2 and 5 hours were taken after immersion. After the 5 hour time point, the animals were returned to their cages and a 24-hour time point was taken to assess the possibility of long-term effects. The effect of pH on barrier recovery also was studied after tape-stripping of flanks to produce TEWL reading between 3.0 and 7.0 mg/cm$^2$/hr.

Figure 1:
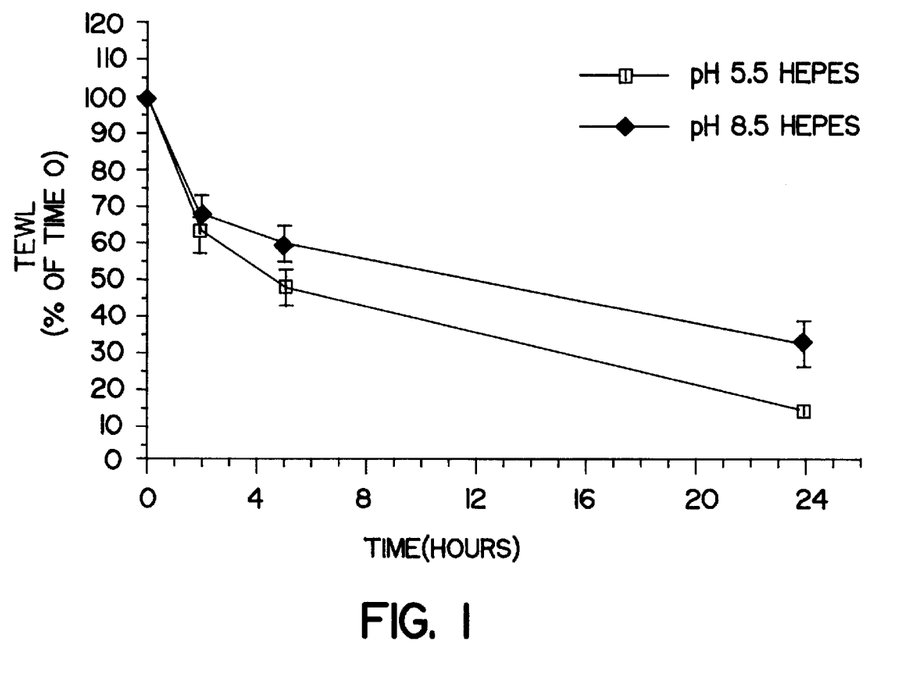
Figure 2:
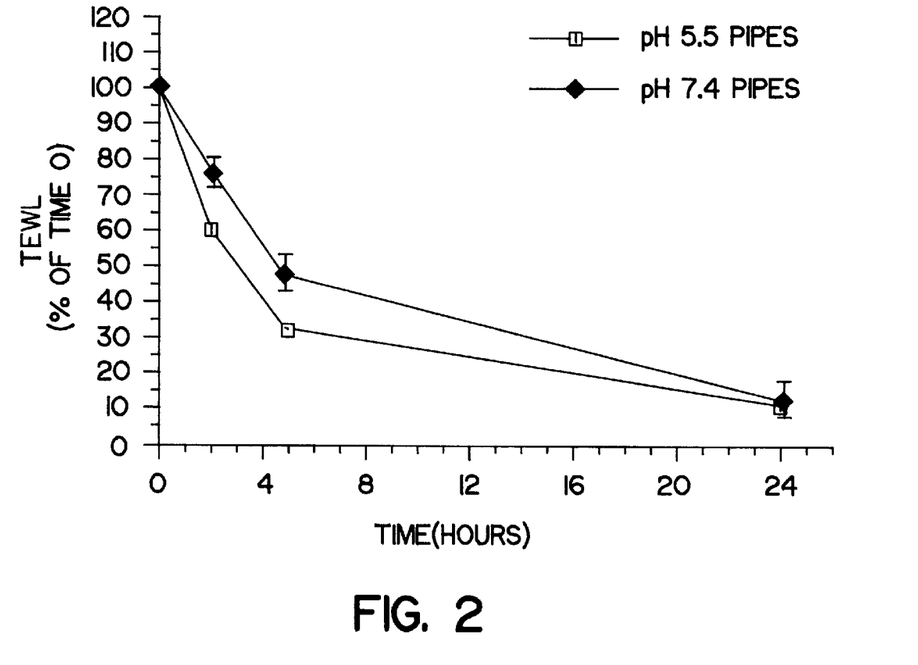
Figure 3:
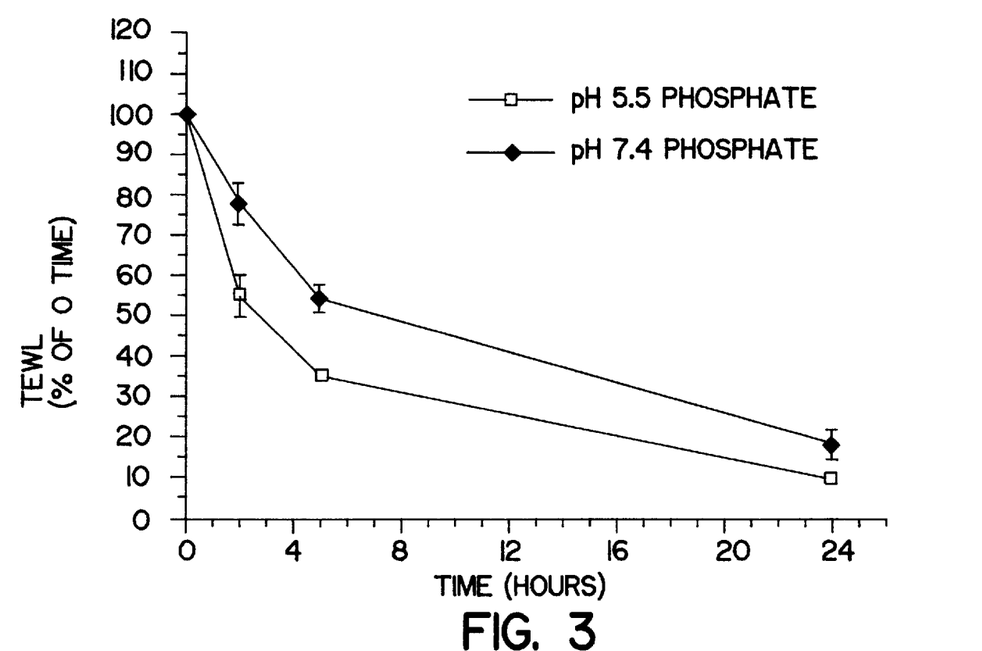
Figure 4:
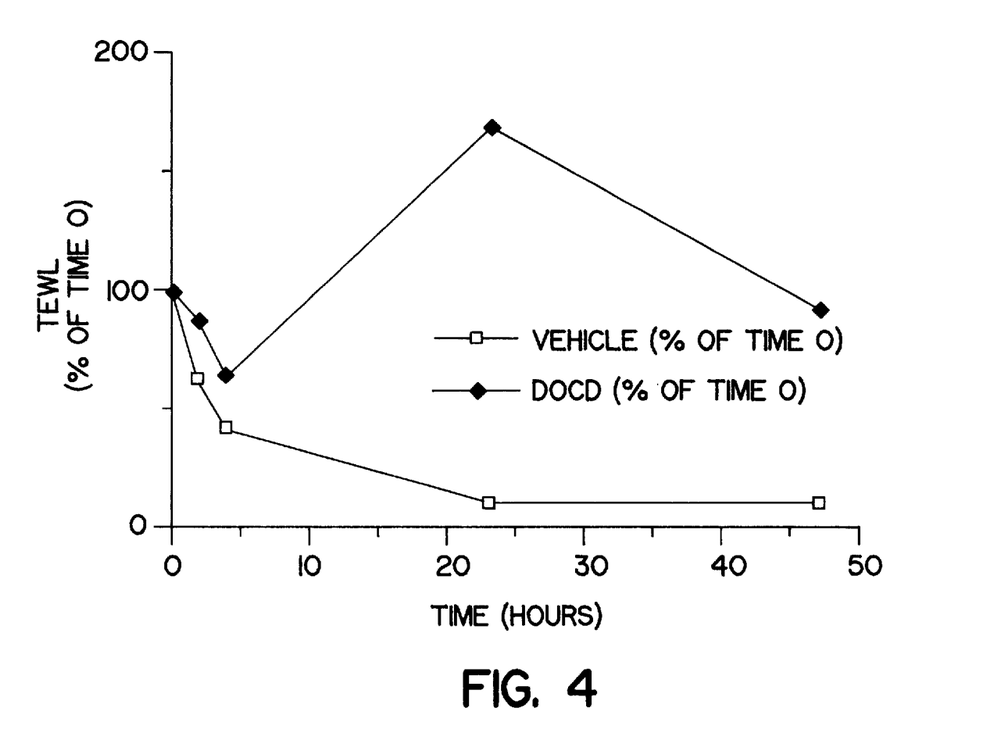
Figure 5:
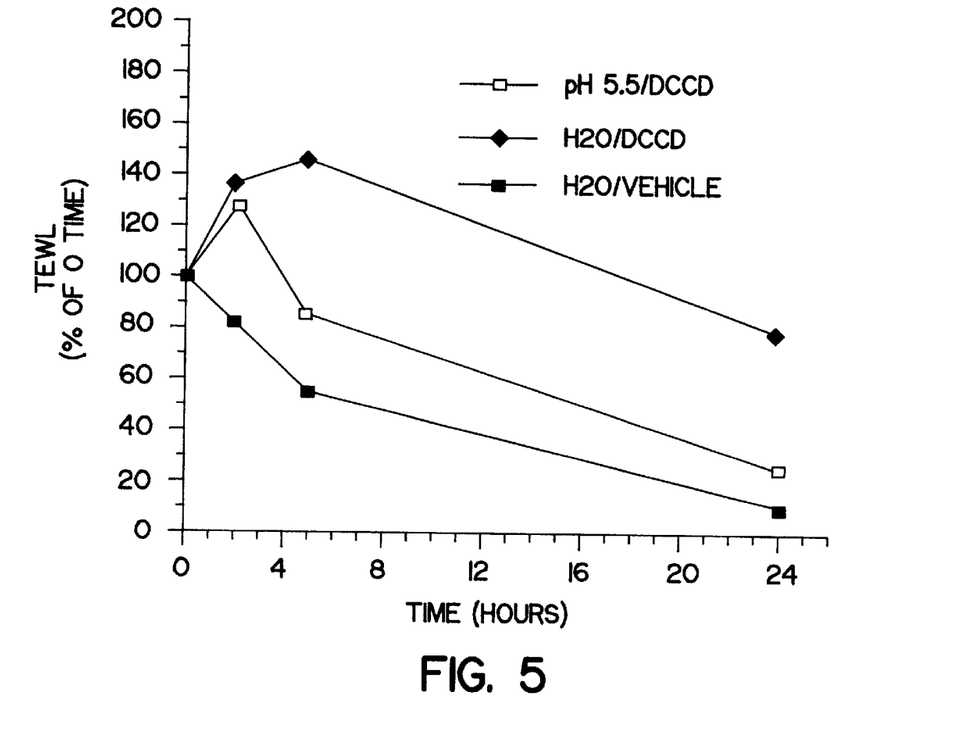
Figure 6:
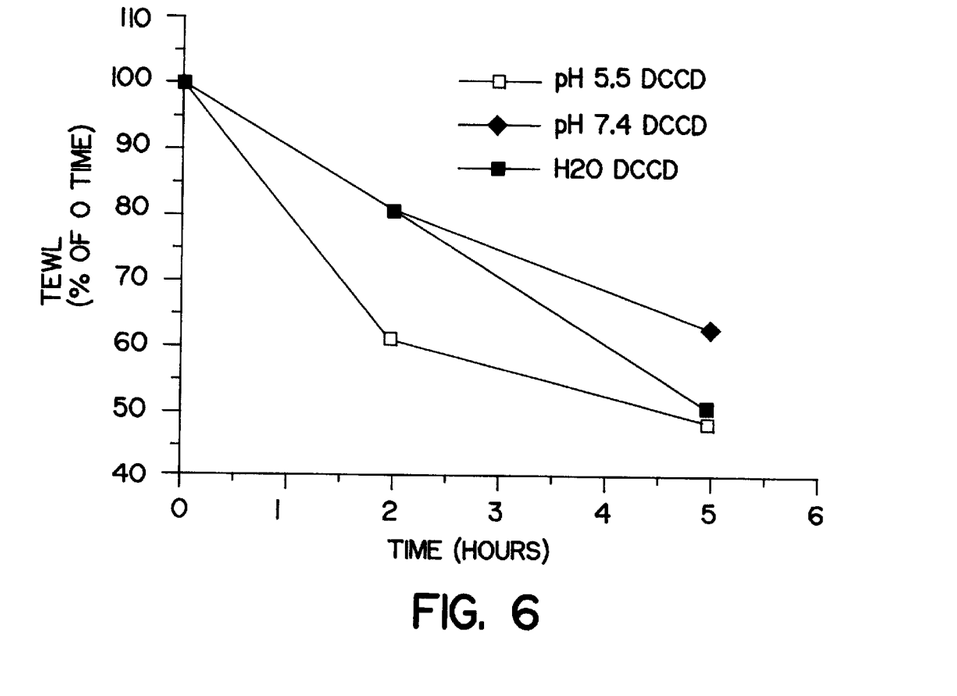

An Evaporimeter (ServoMed) was used to measure TEWL. Test results are shown in FIG. 1 (HEPES), FIG. 2 (PIPES), FIG. 3 (Sodium Phosphate), FIGS. 4–5 (DCCD), and FIG. 6 (DCCD), Tape Stripping).

These data show that immersion of pre-permeabilized skin in either neutral or alkaline buffers causes a significant delay in barrier recovery in comparison to comparable sites immersed in the same buffers at acidic pH's. This is not a toxic effect, because transfer from a neutral or alkaline to an acidic buffer, results in a more rapid rate of recovery, which soon "catches up" to recovery rates in skin exposed to acidic pH only.

EXAMPLE 6

TEWL TOPICAL STUDIES

Proton-pump inhibitors: N,N'-dicyclohexylcarbodiimide (DCCD); 1–10 mM); N-ethyl maleimide (NEM; 1 mM); 7-chloro-4-nitrobenz-2-oxa-1,3-diazole (NBD Cl; 1 mM) and bafilomycin A$_1$ (10 μM) were prepared in vehicle (i.e., 70% propylene glycol, 30% ethanol). Flanks of hairless mice were pre-treated for 30 minutes to 1 hour with drug or vehicle alone before breaking the barrier with acetone. TEWL readings were taken at various time points as described above, followed by additional treatments with drug or vehicle. The DCCD-override study included immersion of flanks in HEPES buffer at pH 5.5 or 7.4 after the pre-treatment with either drug or vehicle and after breaking the barrier with either acetone or by tape stripping.

Figure 7:
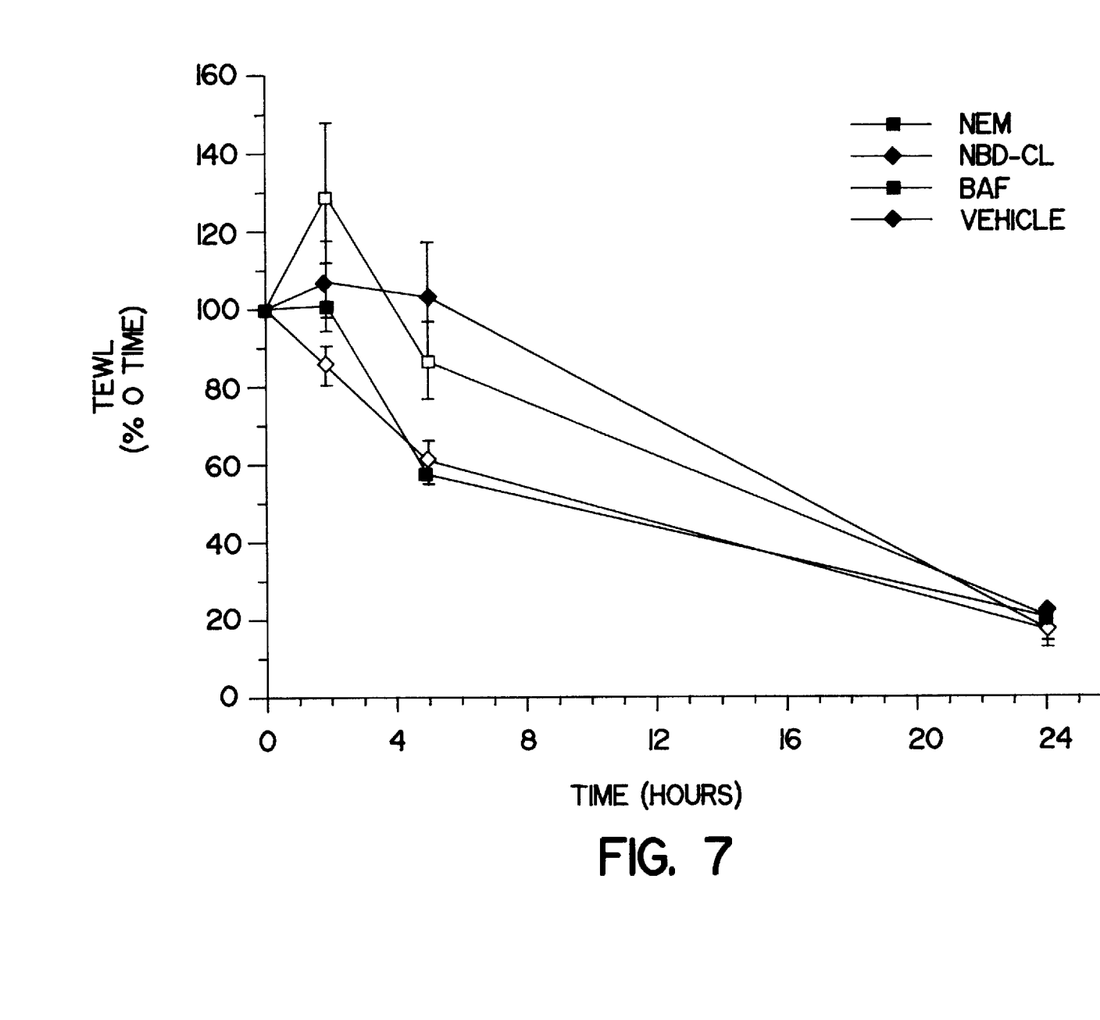

Test results are shown in FIG. 7 (NEM, NBD-chloride, BAF).

These data show that the topical applications of the proton-pump inhibitors tested cause a delay in barrier recovery after solvent prepermeabilization of the stratum corneum. That this effect is not toxic, but due specifically to pump inhibition, is shown by the override studies, in which immersion of DCCD-treated skin in an acidic buffer normalized (corrected) the rate of barrier recovery.

EXAMPLE 7

EFFECT OF SUBSTITUTING CERTAIN COMPLEX OR SYNTHETIC LIPIDS ON BARRIER RECOVERY

| Combination (1:1:1 Molar) | 2 Hrs. | Significance | 4 Hrs. | Significance |
|---|---|---|---|---|
| 1. Vehicle | 76.8 ± 3.1 | — | 66.6 ± 4.5 | — |
| 2. Chol:Cer:LA | 78.9 ± 5.2 | N.S. | 66.0 ± 4.6 | N.S. |
| 3. Chol:Cer:PA | 71.1 ± 4.6 | N.S. | 66.8 ± 4.2 | N.S. |
| 4. EpiChol:Cer:LA | 204.3 ± 32.0 | <0.001 | 119.9 ± 13.4 | <0.001 |
| 5. Chol:Cer:VA | 122.3 ± 9.0 | <0.001 | 93.2 ± 6.9 | <0.01 |
| 6. CholPA:Cer:LA | 133.0 ± 7.2 | <0.001 | 80.7 ± 5.3 | <0.005 |

Chol = cholesterol; Cer = bovine ceramides (Sigma); LA = linoleic acid; EpiChol = epicholesterol (3-α-cholesterol); VA = transvaccenic acid (synthetic oleic acid isomer); PA = palmitic acid; and CholPA = cholesterol palmitate. Vehicle: propylene glycol: ethanol, 7:3 vol/vol.

Hairless mice (n=9–10 animals in each group) were treated first with acetone to break the barrier, and TEWL readings were taken. TEWL in all groups was 100% at 0 hrs., then one application of each lipid mixture (or vehicle—propylene glycol; ethanol, 7:3 vols.) was applied to each treated site.

As shown in Table 1, although barrier recovery occurs normally (vs. vehicle) with both compositions containing the three physiological lipids (combinations 2 and 3), a significant delay in barrier recovery occurs with substitution of either relatively inactive synthetic derivative (epicholesterol or trans-vaccenic acid) (combinations 4 and 5). Moreover, although barrier recovery occurs normally whether LA or PA are used in the three component mixture with cholesterol and ceramide, when the complex precursor CholPA is substituted for Chol, barrier recovery is delayed significantly (combination 6).

EXAMPLE 8

A female hairless mouse, aged 8 weeks, was treated with oleic acid. After oleic acid treatment, epicholesterol, which substitutes for cholesterol, or transvaccenic acid or stearyl amine, both of which substitute for free fatty acid, was applied to the animal.

TEWL (trans-epidermal water loss) was measured before and after treatment at convenient time intervals when the animal was alert. An Evaporimeter (ServoMed) was used.

First, TEWL of the left (LHS) and right (RHS) dorsal sides was measured. Then, the animal was anesthetized by 0.25 ml chloral hydrate (CH) IP injection. At t=0, an aliquot of 30 μl oleic acid solution (5% in propylene glycol/ethanol 7:3 (v/v)) was applied directly to both sides of the animal (~1.5×3 cm) using a Hamilton syringe. Two hours after oleic acid treatment, the TEWL rates of both sides were measured, and the RHS was treated with 30 μl of epicholesterol alone and with transvaccenic acid or stearylamine (1.5% in propylene glycol/ethanol 7:3 (v/v)). TEWL was measured thereafter every 2 or 3 hours.

The mice were kept under anesthesia until the harvest of tissue samples and then sacrificed. At time zero, the tested drug delivery compound listed in Tables 2, 3 and 4 below was applied to the whole treated flank of each mouse. After four hours TEWL was measured again and two drug formulations, one containing lidocaine in a vehicle of a mixture of propylene glycol and ethanol and the other containing Leuteinizing Hormone Releasing Hormone (LHRH) in a vehicle of 60% ethanol, 20% propylene glycol and 20% water. Residual formulation was removed from the skin surface with cotton balls three times and the cotton balls were put into vial #1. Five tape-strippings were conducted at the treated skin sites, and each tape was put into an individual vial numbered 2–6. At the same time, blood was drawn and stored under refrigeration. Urine was collected from the mice during the two hour drug application period and placed into vial #8.

After an additional two hours, the treated skin was cut off, the subcutaneous fat was removed, and the whole skin was placed into vial #7 to which 1 ml of tissue solubilizer was added, and the mixture was allowed to digest overnight at 55° C. The corpse was digested in 100 ml of saponification mix at 55° C. overnight.

For analysis, 10 ml of Scintisafe (30%) Scintillation media (Fisher Scientific, Fairlawn, N.J.) was added to vials 1-6, and 8. The blood samples were centrifuged, and an aliquot of 100–200 μl was placed into vial #9 and 10 ml of Scintisafe (30%) was added. Similar aliquots of the corpse digest were placed into vials #10 and #11. To vials #9, 10, and 11, 100 μl of 30% hydrogen peroxide was added to decolorize the contents for about two hours. Then 16 μl of Scintisafe (30%) and 150 μl of acetic acid were added and the mixture was let stand overnight. All vials were subjected to scintillation counting as described above. The parameters for the vehicle are as follows: TEWL 266±22 (T=4 hours); plasma concentration 0.31±0.03%; total body concentration 13.13±0.83 (% dose/ml plasma); N=14.

EXAMPLE 9

Applying the pH buffer TRIS alone at cutaneous surface physiologic pH 5.5 very significantly (p≦0.001) increased lidocaine delivery and also significantly increased water permeability as shown in Table 2. HEPES alone in a single application at pH 5.4, approached statistical significance (p=0.05–0.10) of increased lidocaine delivery and water permeability. When HEPES was applied hourly to maintain pH 5.5, significant increases in both lidocaine delivery and water permeability resulted, but when applied hourly to maintain pH 7.4, only increased water permeability was significant.

TABLE 2

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| TRIS (pH 5.5) | 3 | 50 mM | 583 ± 109 | 0.003 | 0.51 ± 0.08 | 0.017 | 31.5 ± 7.54 | <.001 |
| HEPES (pH 5.4) | 4 | 20 mM | 360 ± 18 | 0.108 | 0.43 ± 0.07 | 0.096 | 16.08 ± 2.46 | 0.158 |
| HEPES (pH 5.5) hourly application | 5 | 20 mM | 560 ± 125 | 0.003 | 0.38 ± 0.08 | 0.307 | 18.85 ± 2.77 | 0.015 |
| HEPES (pH 7.4) hourly application | 4 | 20 mM | 460 ± 24 | 0.002 | 0.24 ± 0.03 | 0.260 | 12.21 ± 0.96 | 0.585 |

EXAMPLE 10

When the proton pump inhibitor, monensin, was applied with TRIS at pH 7.4, very significantly increased lidocaine delivery and significantly increased water permeability occurred, as shown in Table 3. When the combination of HEPES and monensin were applied at pH 7.4, water permeability was very significantly increased while lidocaine delivery was significantly increased. When this combination was applied hourly, statistically very significant increases in water permeability and lidocaine delivery occurred. When HEPES was applied with DCCD, another proton pump inhibitor, significant delivery only of lidocaine occurred.

Brefeldin A is a molecule that inhibits "proton" granule migration and exocytosis, resulting in the same stratum corneum effects as a proton pump inhibitor. When this compound was applied with either HEPES or TRIS while the pH was held at a basic 7.4, there was a very significant increase only of lidocaine delivery. HEPES very significantly increased water permeability while TRIS significantly increased it.

These two examples show that increasing the epithelial extracellular space pH by topical application of buffers, proton pump inhibitors, or "proton" granule secretory inhibitors alone or in combination prevent normal hydrolysis of precursors of ceramide and free fatty acids, two of the critical lipids comprising the stratum corneum permeability barrier. This results in accumulation of the precursors, inducing phase separation, as well as distorting the critical lipid ratio, thus disrupting the stratum corneum barrier. Increases in stratum corneum permeability to water and lidocaine delivery that ranged from very significant to approaching significance resulted.

EXAMPLE 11

In this study, phase separation of the stratum corneum membrane bilayers was induced by application of one or two inactive synthetic analogs of the critical lipids in a propylene glycol/ethanol vehicle, as shown by very significantly increased delivery of lidocaine. As shown in Table 4, the two combinations of epicholesterol with either transvaccenic acid or stearyl amine produced very significantly increased lidocaine delivery, while epicholesterol alone significantly increased its delivery. Epicholesterol with transvaccenic acid significantly increased water permeability as well.

TABLE 4

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| epicholesterol + transvaccenic acid | 4 | 2.0/1.0 | 124 ± 36 | <.017 | 0.93 ± 14 | <.0001 | 71.31 ± 4.18 | <.0001 |
| epicholesterol | 3 | 2.0 | 397 ± 55 | >.2 | 0.24 ± 0.05 | .004 | 11.40 ± 1.98 | >.2 |
| stearylamine + epicholesterol | 4 | 2.0/0.5 | 238 ± 38 | >.2 | 1.01 ± 0.18 | <.0001 | 59.36 ± 5.65 | <.0001 |

Several specimens were analyzed for LHRH content with RIA to determine the delivery rate of a peptide. As shown in Table 5, the combination of epicholesterol with transvaccenic acid delivered the peptide LHRH at 4.7 times the amount delivered by the vehicle. The combination of epicholesterol with stearylamine delivered the peptide LHRH at 4.3 times the amount delivered by the vehicle.

TABLE 5

| Compounds | Example | LHRH Delivery Ratio vs. Vehicle | SEM |
|---|---|---|---|
| Epicholesterol + Transvaccenic acid | Synthetic Analogs | 4.7 | 2.7 |
| Epicholesterol + Stearylamine | Synthetic Analogs | 4.3 | 1.9 |

The invention having been fully described, it will be apparent to one of ordinary skill in the art that many changes and modifications can be made without departing from the spirit or scope of the invention.

TABLE 3

| Compounds | N | Conc (%) | TEWL (T = 4 hours) | P | Plasma Conc. (% dose/ml plasma) | P | Total Body Conc. (%) | P |
|---|---|---|---|---|---|---|---|---|
| HEPES (pH 7.2) + Monensin hourly application | 4 | 20 mM/0.5 | 645 ± 90 | <.001 | 0.55 ± 0.06 | 0.001 | 54.01 ± 4.80 | <.001 |
| HEPES (pH 7.4) + Monensin | 4 | 20 mM/0.5 | 520 ± 58 | 0.001 | 0.48 ± 0.09 | 0.033 | 17.04 ± 2.11 | 0.055 |
| TRIS (pH 7.4) + monensin | 4 | 50 mM/0.1 | 445 ± 102 | 0.043 | 0.45 ± 0.03 | 0.040 | 22.55 ± 2.97 | <.001 |
| HEPES (pH 7.4) + Brefeldin A | 3 | 20 mM/0.1 | 637 ± 61 | <.001 | 0.43 ± 0.13 | 0.159 | 21.91 ± 1.01 | <.001 |
| TRIS (pH 7.4) + Brefeldin A | 4 | 50 mM/0.1 | 448 ± 13 | 0.004 | 0.67 ± 0.21 | 0.008 | 25.20 ± 4.36 | <.001 |
| HEPES (pH 7.4) + DCCD | 4 | 20 mM/20 mM | 213 ± 28 | 0.140 | 0.37 ± 0.05 | 0.378 | 18.92 ± 0.79 | 0.003 |

We claim:

1. A method for enhancing permeation of a topically administered therapeutic or prophylactic agent in a host in need of the cutaneous or transdermal administration of a therapeutic or prophylactic agent, which comprises the following steps:
    (a) applying to the epithelium of the host, a composition comprising a penetration enhancing compound that is a proton pump inhibitor selected from the group consisting of cholesterol, cholesterol oleate, cholesterol laurate, cholesterol myristate, cholesterol palmitate, cholesterol stearate, cholesterol arachidate, cholesterol sulfate, epicholesterol, cholesterol phosphate, squalene, 7-dehydrocholesterol, lanosterol, desmosterol, and zymolsterol, in a penetration enhancing amount within the range of from about 0.01 to about 25 weight percent; and (b) applying to the epithelium of the host a therapeutic or prophylactic agent;

said penetration enhancing compound thereby causing enhanced permeation of the therapeutic or prophylactic agent through the epithelium.

2. The method according to claim 1 wherein the penetration enhancing compound is cholesterol or cholesterol sulfate.

3. The method according to claim 1 wherein the application is in the form of a topical composition.

4. The method according to claim 3, wherein the topical composition is a cream or ointment.

5. The method according to claim 1, wherein the composition further contains a known epithelial penetration enhancer selected from the group consisting of 1-dodecylazacycloheptan-2-one, propylene glycol, oleyl alcohol, and methyl pyrrolidone.

6. The method of claim 1 wherein the therapeutic or prophylactic agent is selected from the group consisting of estradiol valerate, indomethacin, nifedipine, oxymorphone, lidocaine and LHRH.

7. The method of claim 1 wherein the therapeutic or prophylactic agent is LHRH.

8. The method of claim 1 wherein the therapeutic or prophylactic agent is lidocaine.

9. The method of claim 1 wherein the therapeutic or prophylactic agent is oxymorphone.

10. The method of claim 1 wherein the therapeutic or prophylactic agent is indomethacin.

11. The method of claim 1 wherein the therapeutic or prophylactic agent is estradiol valerate.

12. The method of claim 1 wherein the therapeutic or prophylactic agent is nifedipine.

* * * * *